(12) United States Patent
Braga et al.

(10) Patent No.: US 8,979,744 B2
(45) Date of Patent: Mar. 17, 2015

(54) TUNNELING SYSTEM

(75) Inventors: Richard Braga, Taunton, MA (US); Mark Callahan, Medway, MA (US); Todd Chelak, Westborough, MA (US); Brett Haarala, Framingham, MA (US)

(73) Assignee: Covidien LP, Mansfield, MA (US)

( * ) Notice: Subject to any disclaimer, the term of this patent is extended or adjusted under 35 U.S.C. 154(b) by 1454 days.

(21) Appl. No.: 12/206,391

(22) Filed: Sep. 8, 2008

(65) Prior Publication Data

US 2010/0063513 A1 Mar. 11, 2010

(51) Int. Cl.
*A61B 1/00* (2006.01)
*A61M 25/01* (2006.01)
*A61B 17/32* (2006.01)
*A61B 17/00* (2006.01)

(52) U.S. Cl.
CPC .......... *A61M 25/0194* (2013.01); *A61B 17/32* (2013.01); *A61B 2017/00477* (2013.01); *A61B 2017/320056* (2013.01); *A61M 25/0102* (2013.01)
USPC ...................................... 600/184; 604/164.01

(58) Field of Classification Search
USPC ......... 600/184; 606/108; 604/164.01–164.07, 604/96.01, 533–539, 523, 174–180, 44, 43, 604/6.16; 403/384, 339, 340, 331
See application file for complete search history.

(56) References Cited

U.S. PATENT DOCUMENTS

| 4,299,228 A | 11/1981 | Peters |
|---|---|---|
| 4,490,136 A | 12/1984 | Ekbladh et al. |
| 4,574,806 A * | 3/1986 | McCarthy ................ 606/108 |
| 4,674,496 A | 6/1987 | Svadjian et al. |
| 4,705,041 A | 11/1987 | Kim |
| 4,819,694 A | 4/1989 | Jiang |
| 4,832,687 A | 5/1989 | Smith |
| 5,059,170 A | 10/1991 | Cameron |
| 5,129,891 A | 7/1992 | Young |
| 5,207,643 A | 5/1993 | Davis |
| 5,209,723 A | 5/1993 | Twardowski et al. |
| 5,279,597 A | 1/1994 | Dassa et al. |
| 5,358,506 A | 10/1994 | Green et al. |
| 5,405,320 A | 4/1995 | Twardowski et al. |
| 5,478,318 A | 12/1995 | Yoon |
| 5,505,714 A | 4/1996 | Dassa et al. |
| 5,509,897 A | 4/1996 | Twardowski et al. |
| 5,562,618 A | 10/1996 | Cai et al. |
| 5,613,945 A | 3/1997 | Cai et al. |
| 5,624,413 A | 4/1997 | Markel et al. |
| 5,632,729 A | 5/1997 | Cai et al. |
| 5,637,102 A | 6/1997 | Tolkoff et al. |
| 5,718,678 A | 2/1998 | Fleming, III |
| 5,743,873 A | 4/1998 | Cai et al. |
| 5,797,869 A * | 8/1998 | Martin et al. ............. 604/43 |

(Continued)

OTHER PUBLICATIONS

Polycath, Polyurethane Central Venous Catheter CVC 100-50, CVC 100-65, CVC 200-60, CVC 200-68.

(Continued)

*Primary Examiner* — Darwin Erezo
*Assistant Examiner* — Katrina Stransky
(74) *Attorney, Agent, or Firm* — John Paul Mello, Esq.

(57) ABSTRACT

A tunneling system includes an elongate tunneling member defining a longitudinal axis along at least a portion of a longitudinal length thereof. The elongate tunneling member has a first end and a second end. The second end of the elongate tunneling member includes a coupling segment adapted for securely engaging a catheter.

6 Claims, 17 Drawing Sheets

(56) References Cited

U.S. PATENT DOCUMENTS

| | | |
|---|---|---|
| 5,944,732 A | 8/1999 | Raulerson et al. |
| 6,099,519 A | 8/2000 | Olsen et al. |
| 6,113,572 A | 9/2000 | Gailey et al. |
| 6,126,631 A | 10/2000 | Loggie |
| 6,423,053 B1 | 7/2002 | Lee |
| 6,453,185 B1 | 9/2002 | O'Keefe |
| 6,638,242 B2 | 10/2003 | Wilson et al. |
| D498,844 S | 11/2004 | Diamond et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,916,051 B2 | 7/2005 | Fisher |
| 6,921,396 B1 | 7/2005 | Wilson et al. |
| 6,939,328 B2 | 9/2005 | Raulerson |
| 6,969,381 B2 | 11/2005 | Voorhees |
| 6,979,339 B2 | 12/2005 | Bishop et al. |
| 7,008,395 B1 | 3/2006 | Loggie |
| 7,087,071 B2 | 8/2006 | Nicholas et al. |
| 7,128,734 B1 | 10/2006 | Wilson et al. |
| 7,144,409 B2 | 12/2006 | Aranyi |
| 7,163,531 B2 | 1/2007 | Seese et al. |
| 7,261,708 B2 | 8/2007 | Raulerson |
| 7,300,430 B2 | 11/2007 | Wilson et al. |
| 7,578,803 B2 * | 8/2009 | Rome et al. ............... 604/167.04 |
| 7,955,318 B1 * | 6/2011 | Schultz et al. ................ 604/540 |
| 2004/0034324 A1 | 2/2004 | Seese et al. |
| 2004/0044330 A1 * | 3/2004 | Li et al. ......................... 604/535 |
| 2004/0065333 A1 | 4/2004 | Wilson et al. |
| 2004/0167478 A1 | 8/2004 | Mooney et al. |
| 2004/0171997 A1 | 9/2004 | Wilson et al. |
| 2004/0176739 A1 | 9/2004 | Stephens et al. |
| 2004/0176788 A1 * | 9/2004 | Opolski ........................ 606/167 |
| 2004/0210187 A1 * | 10/2004 | Zawacki ......................... 604/43 |
| 2005/0085765 A1 | 4/2005 | Voorhees |
| 2005/0107770 A1 | 5/2005 | Schweikert et al. |
| 2005/0137580 A1 | 6/2005 | Raulerson et al. |
| 2005/0209583 A1 | 9/2005 | Powers et al. |
| 2005/0209584 A1 | 9/2005 | Rome |
| 2005/0228364 A1 | 10/2005 | Braga |
| 2005/0256461 A1 * | 11/2005 | DiFiore et al. ................ 604/247 |
| 2005/0261665 A1 | 11/2005 | Voorhees |
| 2006/0009783 A1 | 1/2006 | Rome et al. |
| 2006/0015086 A1 | 1/2006 | Rasmussen et al. |
| 2006/0015130 A1 * | 1/2006 | Voorhees et al. ............. 606/190 |
| 2006/0095062 A1 | 5/2006 | Stephens |
| 2006/0135949 A1 | 6/2006 | Rome et al. |
| 2006/0224110 A1 | 10/2006 | Scott et al. |
| 2006/0276773 A1 | 12/2006 | Wilson et al. |
| 2007/0016167 A1 | 1/2007 | Smith et al. |
| 2007/0049960 A1 | 3/2007 | Stephens et al. |
| 2007/0060866 A1 | 3/2007 | Raulerson et al. |
| 2007/0078396 A1 * | 4/2007 | Feeley et al. ............. 604/164.01 |
| 2007/0260221 A1 | 11/2007 | Chesnin |
| 2007/0265597 A1 | 11/2007 | Schweikert et al. |
| 2007/0282274 A1 | 12/2007 | Chesnin |
| 2008/0009832 A1 | 1/2008 | Barron et al. |
| 2008/0051863 A1 * | 2/2008 | Schneider et al. ............ 607/126 |
| 2008/0086161 A1 | 4/2008 | Massengale et al. |
| 2008/0097409 A1 | 4/2008 | Stephens |
| 2008/0214992 A1 | 9/2008 | Haarala et al. |

OTHER PUBLICATIONS

"Aspira* Pleural Drainage System", Bard Access Systems, Inc., Salt Lake City, Utah, Instruction Manual dated Oct. 2007.

"Aspira* Pleural Drainage Catheter", Bard Access Systems, Inc., Product Description and Instruction Manual (undated).

"Aspira* Pleural Drainage System—Compassionate Treatment", Bard Access Systems, Inc., Product Description Article (undated).

"Aspira* Pleural Drainage System Product Features", Bard Access Systems, from website http://www.myaspira.com/pages/clinchoose.html.

European Patent Search Report dated Dec. 21, 2011 issued in European Patent Application No. EP 11 183 344.

* cited by examiner

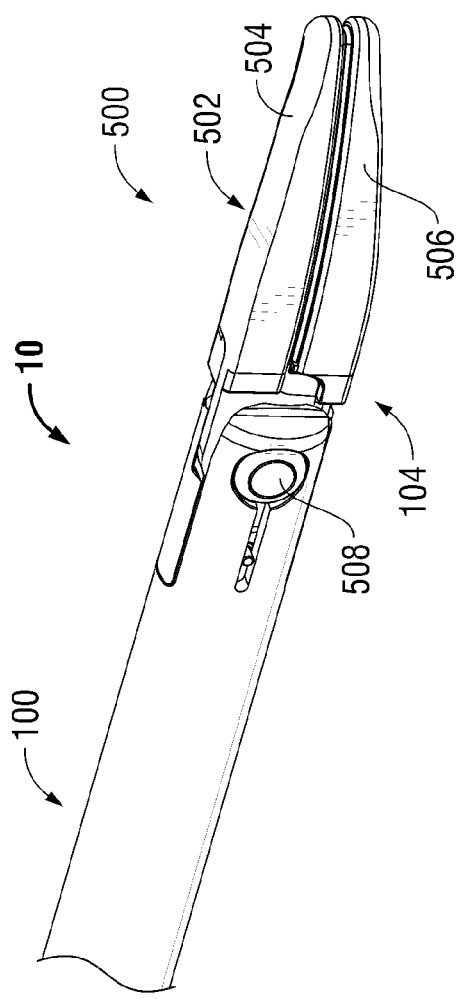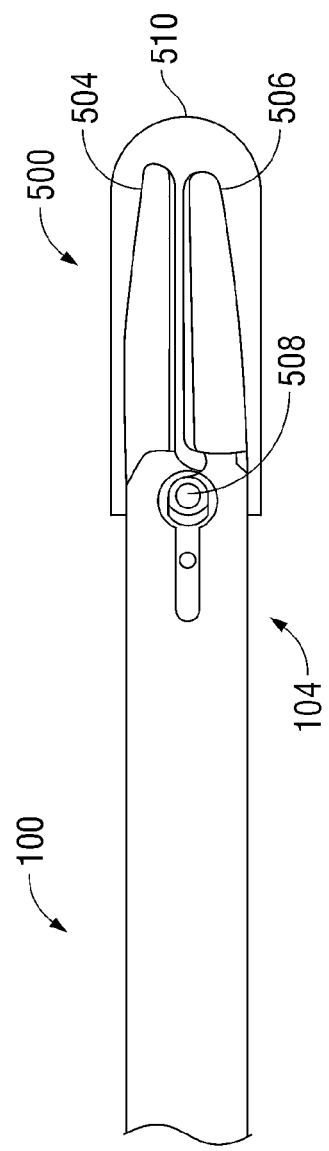
FIG. 3A
FIG. 3B

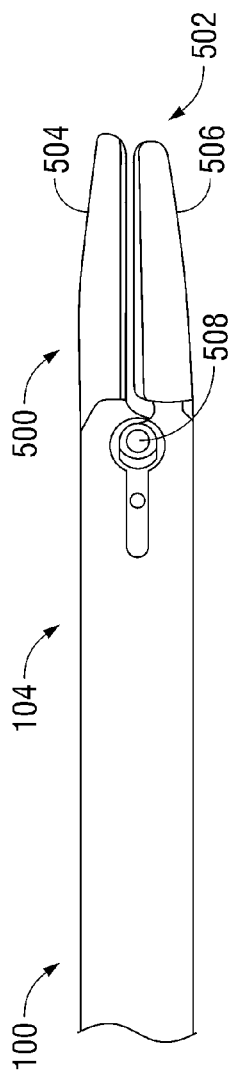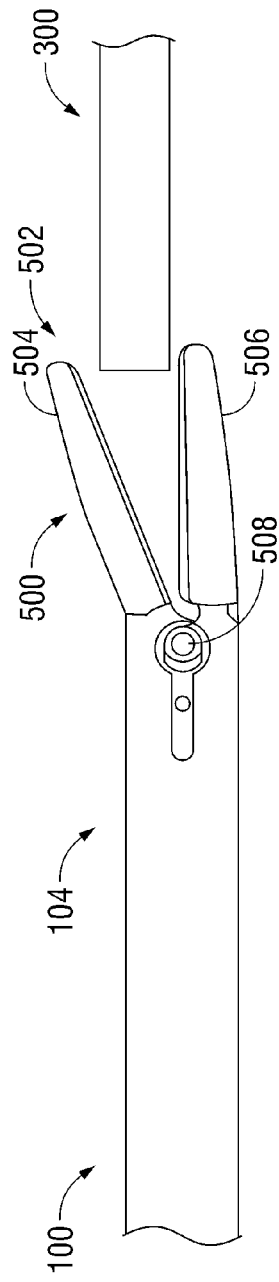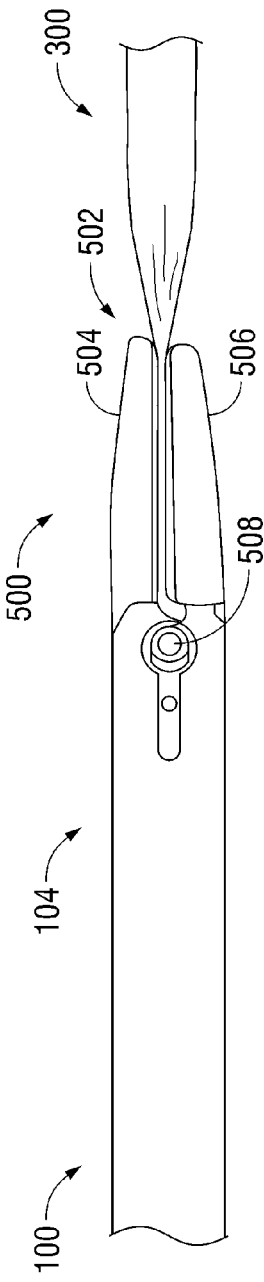

TUNNELING SYSTEM

BACKGROUND

1. Technical Field

The present disclosure relates generally to a tunneling system, and, more particularly, relates to a tunneling system connectable to a catheter.

2. Description of the Related Art

Catheters are flexible instruments intended for the withdrawal and introduction of fluids relative to body cavities, ducts, and vessels. Catheters have particular application in hemodialysis procedures where blood is withdrawn from a blood vessel for treatment and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste, and toxins. The dialyzed blood is returned to the subject through a venous lumen of the catheter.

Various devices are employed for the insertion of hemodialysis catheters including, e.g., tunnelers, introduction stylets or the like. A known technique of inserting a catheter includes forming a subcutaneous tunnel between two spaced openings in the skin with the use of a trocar or the like. The catheter end is attached to the insertion stylet or trocar and pulled though the tunnel to expose the catheter which is subsequently inserted into, e.g., the jugular vein or other vessel, and routed to the heart. The catheter end must be secured to the trocar in a manner which prevents detachment during passage through the tissue. In addition, the profile of the insertion devices and catheter may need to be minimized for ease of passage through the subcutaneous tissue. Adaptability of a broad range of catheters, tunnelers and sheaths is also a consideration.

SUMMARY

Accordingly, the present disclosure is directed to a tunneling system for use with a catheter having at least one longitudinal lumen. The tunneling system includes an elongate tunneling member defining a longitudinal axis along at least a portion of a longitudinal length thereof. The elongate tunneling member has a first end and a second end. The second end of the elongate tubular member includes a coupling segment adapted for securely engaging a catheter. The second end of the elongate tubular member may incorporate different embodiments of couplings segments. For example, the coupling segment may include at least one pin extending radially with respect to the longitudinal axis. The pin is adapted to be received within at least one hole of the catheter. Other embodiments are also envisioned.

BRIEF DESCRIPTION OF THE DRAWINGS

Embodiments of the present disclosure will be better understood with reference to the accompanying drawings, wherein:

FIG. 3A is a perspective view of another alternate embodiment of the tunneling system including a clamping member with a pair of jaws;

FIG. 3B is a side plan view of the tunneling system shown in FIG. 3A with a sheath covering the coupling;

FIG. 3C is a side plan view of the tunneling system of FIG. 3A illustrating the jaws of the coupling in the closed position;

FIG. 3D is a side plan view of the tunneling system of FIG. 3A illustrating the jaws of the coupling in an open position with a catheter positioned adjacent the coupling;

FIG. 3E is a side plan view of the tunneling system of FIG. 3A depicting the jaws of the coupling clasping the catheter;

DETAILED DESCRIPTION OF THE EMBODIMENTS

The exemplary embodiments of the present disclosure are directed to a tunneling system incorporating a coupling adapted for connection to a catheter. The tunneling system of the present disclosure may have various applications. During a hemodialysis catheter implantation procedure, the tunneling system creates or enlarges a subcutaneous tunnel within a subject and positions a catheter in the target site. It is envisioned, however, that the presently disclosed tunneling system may be employed in other suitable medical procedures. For instance, the tunneling system of the present disclosure may be utilized for subcutaneously implanting a stent, a vascular graft, or the like, inside a subject's body.

In the discussion that follows, the term "clinician" refers to a doctor, a nurse, or any other care provider and may include support personnel. The term "proximal" will refer to the portion of a structure that is closer to a clinician, whereas the term "distal" will refer to the portion that is farther from the clinician.

Figure 1A:
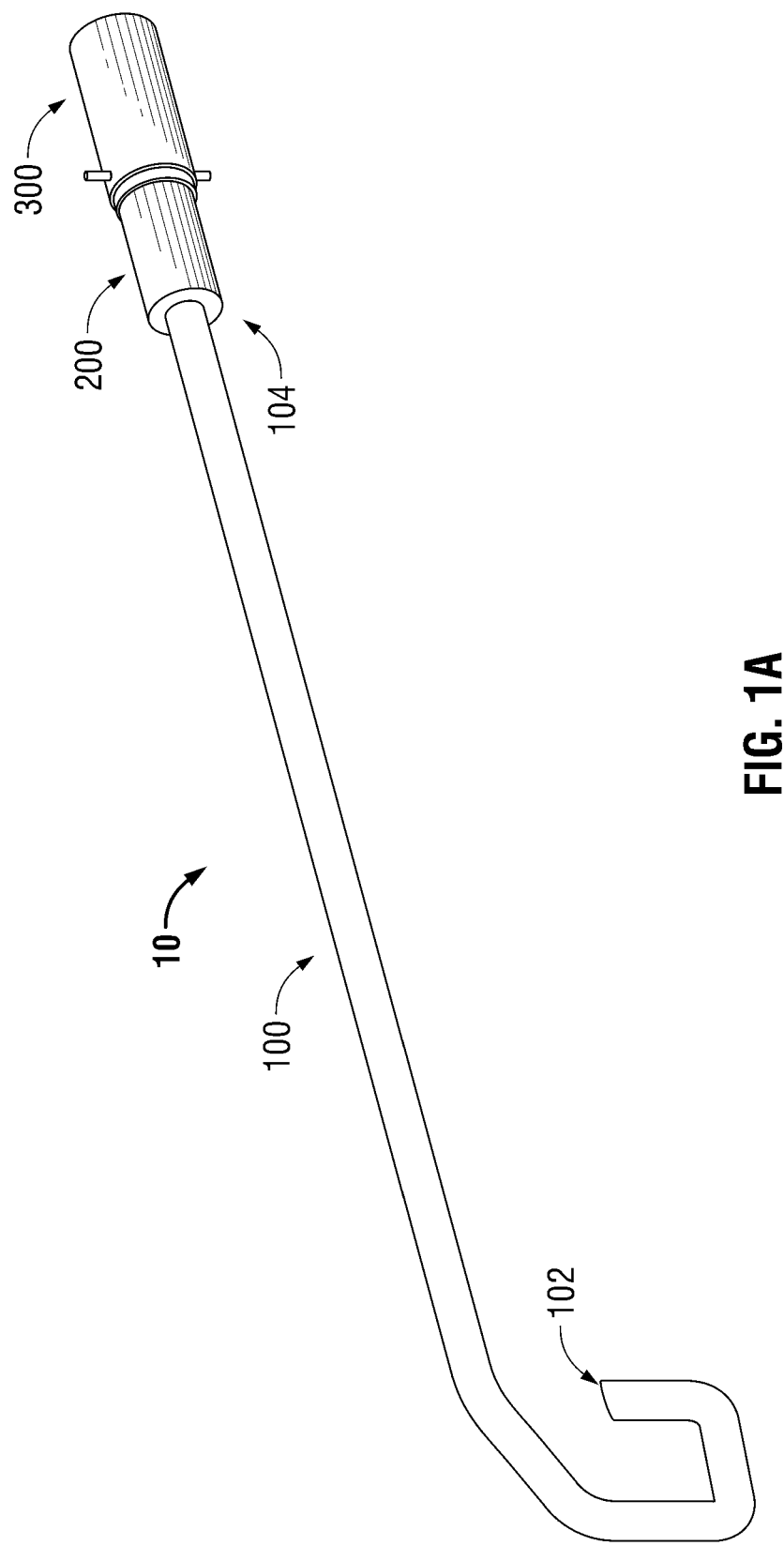
FIG. 1A is a perspective view of a tunneling system illustrating an elongate tunneling member and a coupling for releasably connecting a catheter.

Referring now in detail to the drawings where like reference numerals identify similar or like components throughout the several view, FIG. 1A generally illustrates the tunneling system 10 of the present disclosure. In brief, tunneling system 10 includes an elongate tunneling member 100 operatively connected to or integrally formed with a coupling 200. In operation, the elongate tunneling member 100 serves to create or enlarge subcutaneous tunnel within a subject. The coupling 200 is capable of securely engaging a catheter 300. Once coupling 200 has been secured to catheter 300, a clinician can maneuver catheter 300 within the subcutaneous tunnel formed by elongate tunneling member 100 through cooperative movement of the elongate tunneling member 100. As a result, tunneling system 10 facilitates the placement of the catheter 300 inside a subject at any predetermined location. A clinician employing tunneling system 10 may use the antegrade and reverse tunneling methods disclosed in U.S. Pat. No. 5,509,897 to Twardowski to situate catheter 300 in the desired location. The entire contents of U.S. Pat. No. 5,509,897 are incorporated by reference herein.

Elongate tunneling member 100 of tunneling system 10 defines a longitudinal axis along at least a portion of a longitudinal length thereof and has first end 102 and second end 104. First end 102 of elongate tunneling member 100 is adapted for grasping engagement and handling by a clinician. Second end 104 of elongate tunneling member 100 incorporates or is connected to coupling 200, which is connectable to catheter 300.

Figure 1B:
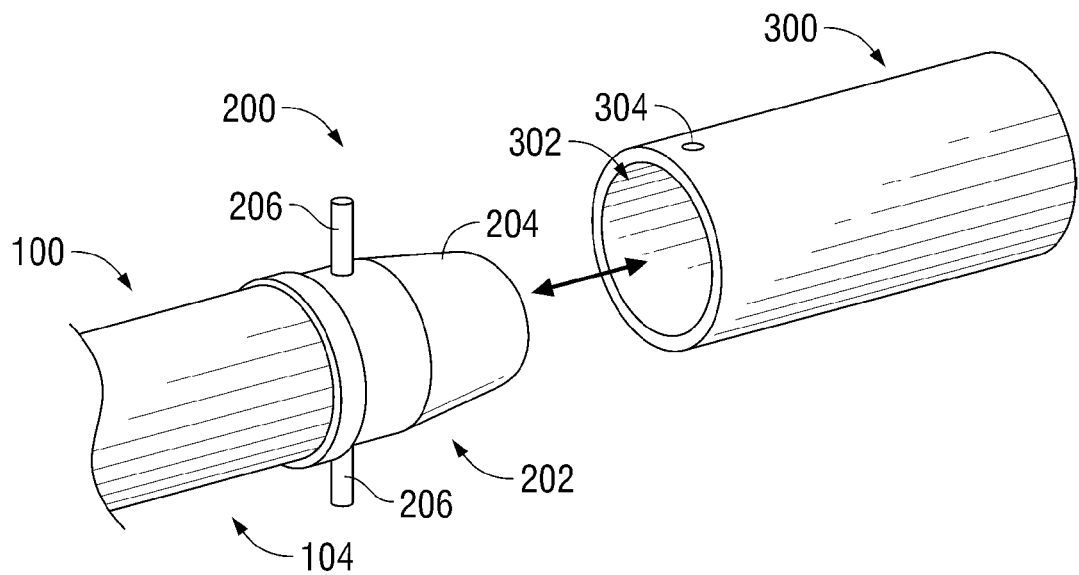
FIG. 1B is an enlarged perspective view of the tunneling system shown in FIG. 1A with a coupling having two radially depending pins and a catheter.
Figure 1C:
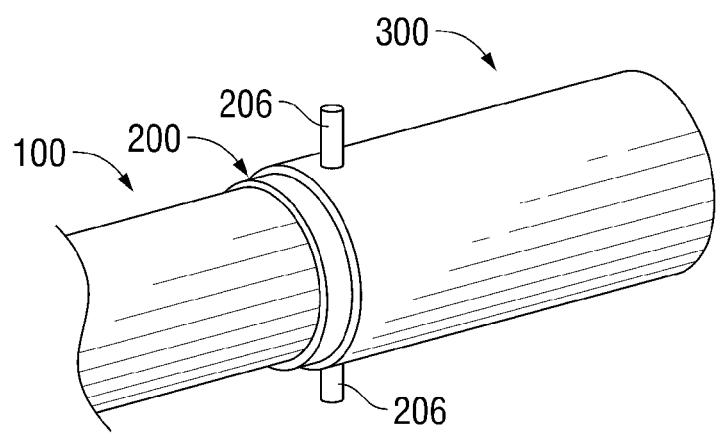
FIG. 1C is an enlarged perspective view of the coupling depicted in FIG. 1B attached to the catheter.
Figure 1D:
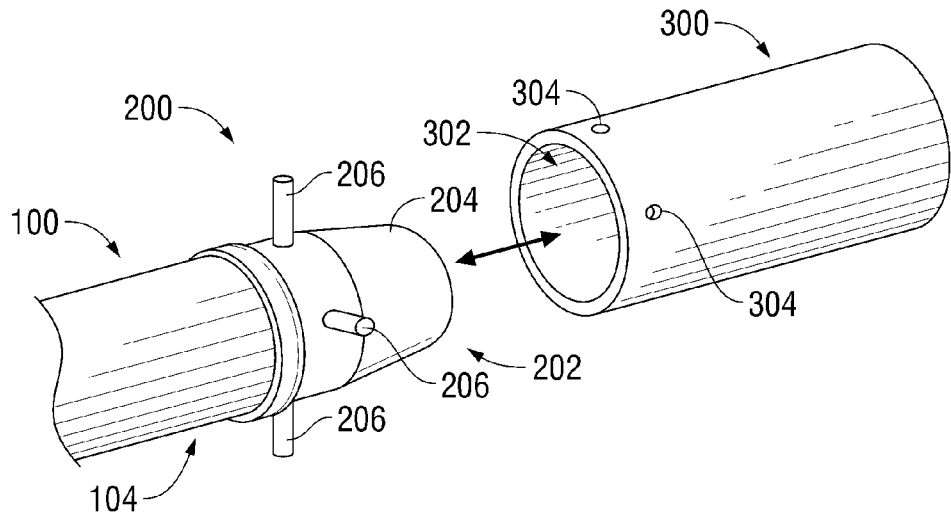
FIG. 1D is an enlarged perspective view of the tunneling system shown in FIG. 1A with a coupling having three radially depending pins.
Figure 1E:
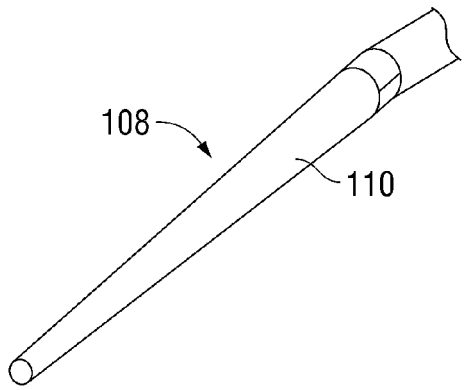
FIG. 1E is an enlarged perspective view of a portion of an alternative embodiment of the tunneling system incorporating an end adapted to create or a enlarge a subcutaneous tunnel.

In an alternate embodiment, elongate tunneling member 100 includes first end 108 configured for passage through tissue to create and/or enlarge a subcutaneous tunnel within a subject, as shown in FIG. 1E. First end 108 includes offset segment 110 dimensioned to facilitate passage through the subcutaneous tunnel. Offset segment 110 may incorporate any angular or arcuate arrangement suitable to facilitate insertion and/or passage through the tissue when elongate tunneling member 100 is manipulated by the clinician. In one embodiment, offset segment 110 is obliquely arranged with respect to the longitudinal axis of the elongate tunneling member 100 at a relatively small angle. Other arrangements and angular relationships of offset segment 110 are also envisioned.

As seen in FIGS. 1A-1C, coupling 200 includes body 202 dimensioned for reception inside longitudinal bore 302 of catheter 300. Body 202, which may have a substantially cylindrical cross-section, includes a tapered distal portion 204 and at least one pin 206 extending radially with respect to coupling 200. Tapered distal portion 204 facilitates insertion of coupling 200 within the longitudinal bore 302 of catheter 300. Pins 206 are adapted to be received by holes 304 of catheter 300. In the embodiment shown in FIG. 1B, body 202 includes two pins 206 positioned in a diametrically opposed relation to each other. Although FIG. 1B shows only two pins 206, body 202 may include fewer or more pins arranged in any suitable configuration, insofar as the pins are capable of permanently or temporarily facilitating connection between coupling 200 and catheter 300. Alternatively, body 202 may include third pin 206 radially spaced apart from remaining pins 206, as illustrated in FIG. 1D. Third pin 206 is also adapted to be received by hole 304 of catheter 300.

To connect catheter 300 to coupling 200, clinician inserts at least a portion of body 202 inside longitudinal bore 302. While the clinician introduces body 202 into longitudinal bore 302, pins 206 bend to permit insertion of body 202. When pins 206 are aligned with holes 304 of catheter 300, the pins 206 return to their original radially outward positions and extend through holes 304. In this arrangement, coupling 200 establishes a secured coupling with catheter 300. The clinician may move or maneuver catheter 300 through a subcutaneous tunnel by controlling the movement of elongate tunneling member 100.

Figure 2:
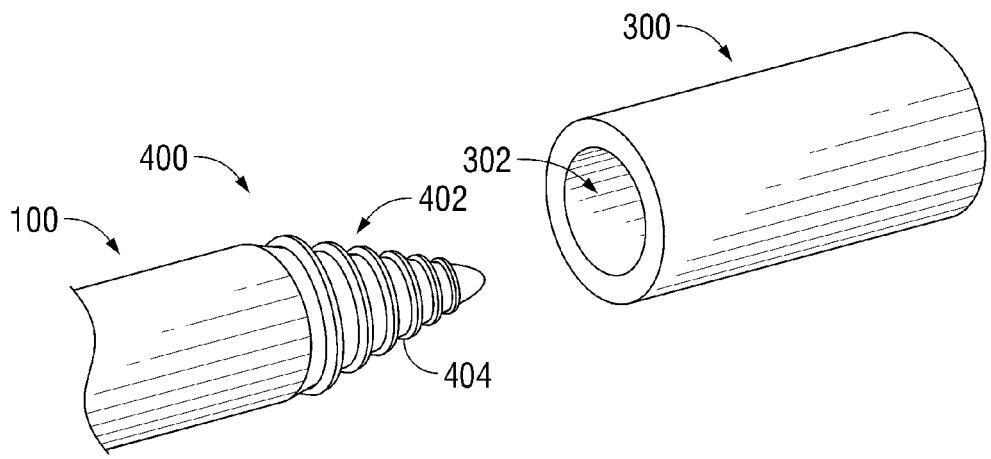
FIG. 2 is an enlarged perspective view of an alternate embodiment of the tunneling system incorporating a coupling with a thread for releasably connecting a catheter.

With reference to FIG. 2, another embodiment of tunneling system 10 includes a coupling 400 having tapered tip 402 dimensioned for insertion into longitudinal bore 302 of catheter 300. Tapered tip 402 defines external thread 404. Thread 404 may define a helical configuration and may be relatively sharp to "bite into" the internal surface portions defining longitudinal bore 302 of catheter 300. As such, thread 404 frictionally engages the internal surfaces portion defining longitudinal bore 302 when inserted into catheter 300. The pitch, shape, and general configuration of tapered tip 402 controls the force needed to connect or disconnect coupling 400 from catheter 300. In one embodiment, the configuration of tapered tip 402 allows the clinician to disconnect coupling 400 from catheter 300 by pulling tunneling member 100 away from catheter 300. Thread 404 may alternatively define an undulating configuration to facilitate engagement with the internal surface portions defining longitudinal bore 302 of catheter 300. In the alternative, catheter 300 may include an internal thread for engaging thread 404.

In use, the clinician positions tapered tip 402 within longitudinal bore 302 of catheter 300. The clinician may rotate elongate tunneling member 100 during this insertion. As the clinician rotates elongate tunneling member 100, thread 404 frictionally engages or bites the internal surfaces defined by the longitudinal lumen 302. When tapered tip 402 is properly positioned within longitudinal bore 302, coupling 400 secures catheter 300 to elongate tunneling member 100. After connecting elongate tunneling member 100 to catheter 300, the clinician can maneuver catheter 300 within a subcutaneous tunnel by directing the motion of elongate tunneling member 100.

Referring now to FIGS. 3A-3E, another embodiment of tunneling system 10 includes coupling 500 located on second end 104 of elongate tunneling member 100. Coupling 500 incorporates clamping member 502 configured for holding an end of catheter 300. Clamping member 502 contains first and second jaws 504, 506 which are pivotally connected to each other. Pivot pin 508, or any other suitable means, connects first jaw 504 to second jaw 506. First jaw 504 moves relative to second jaw 506 between an open position (see FIG. 3D) and a closed position (see FIG. 3E). In the depicted embodiment, first jaw 504 pivots with respect to second jaw 506, while second jaw 506 remains stationary. Notwithstanding the foregoing, other embodiments of clamping member 502 may include stationary first jaw 504 and pivotable second jaw 506, two movable jaws 504, 506, or any other suitable apparatus capable of clamping an end of catheter 300 or a portion of a septum internally dividing catheter 300. Optionally, a protective sheath or wrap 510 may cover clamping member 502 to protect coupling 500 from contamination before usage. The clinician may remove wrap 510 before employing tunneling system 10. Any mechanisms for effecting relative pivotal movement of first and second jaws 502, 504 are envisioned including the embodiments disclosed in commonly assigned U.S. Pat. Nos. 5,358,506, 7,087,071 and 7,144,409, the entire contents of each being hereby incorporated herein by reference.

Figure 3F:
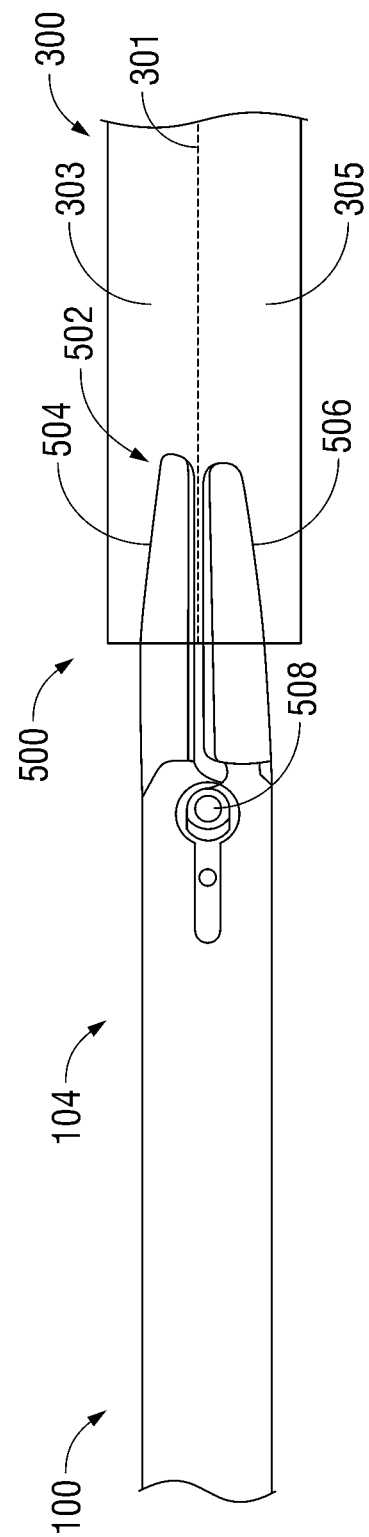
FIG. 3F is a side plan view of the tunneling system of FIG. 3A depicting the jaws of the coupling clasping a septum of the catheter.

During operation, the clinician repositions first and second jaws 504, 506 from a closed position (see FIG. 3C) to an open position (see FIG. 3D). While the jaws 504, 506 are in the open position, the clinician approximates clamping member 502 to an end of catheter 300 until the end of the catheter 300 is positioned between first and second jaws 504, 506, as seen in FIG. 3D. Thereafter, the clinician moves first and second jaws 504, 506 to the closed position to clamp the end of catheter 300, as shown in FIG. 3E. At this moment, coupling 500 properly secures elongate tunneling member 100 to catheter 300. The secured interconnection between elongate tunneling member 100 and catheter 300 allows the clinician to direct the movement of catheter 300 through elongate tunneling system 100. Alternatively, at least a portion of coupling 500 may be inserted within the lumens 303, 305 of a dual-lumen catheter 300 to secure elongate tunneling member 100 to catheter 300, as illustrated in FIG. 3F. In the procedure depicted in FIG. 3F, the clinician introduces each jaw 504, 506 inside one lumen 303, 305 while jaws are located in the open position. Subsequently, the clinician moves jaws 504, 506 to the closed position to grasp septum 301 dividing lumens 303, 305 of catheter 300.

Figure 4A:
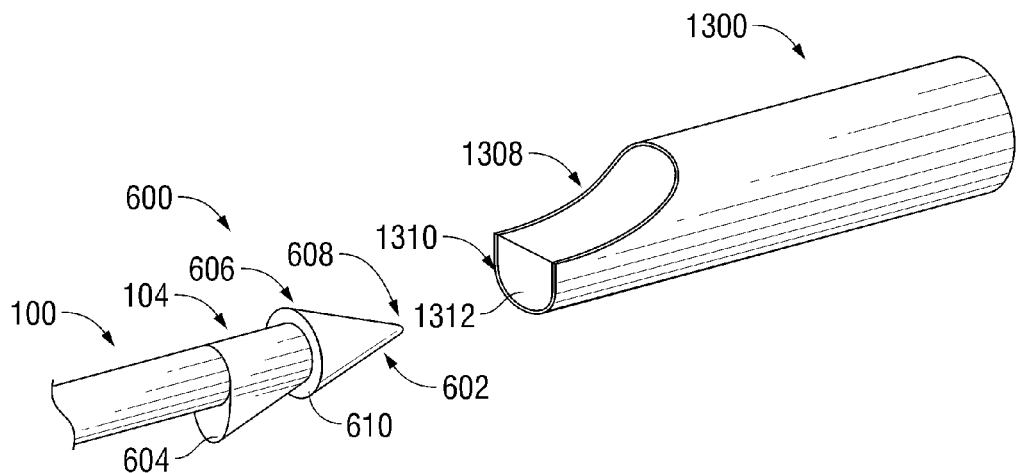
FIG. 4A is an enlarged perspective view of another embodiment of the tunneling system illustrating a coupling incorporating a pointed end and a barb extending radially therefrom.
Figure 4B:
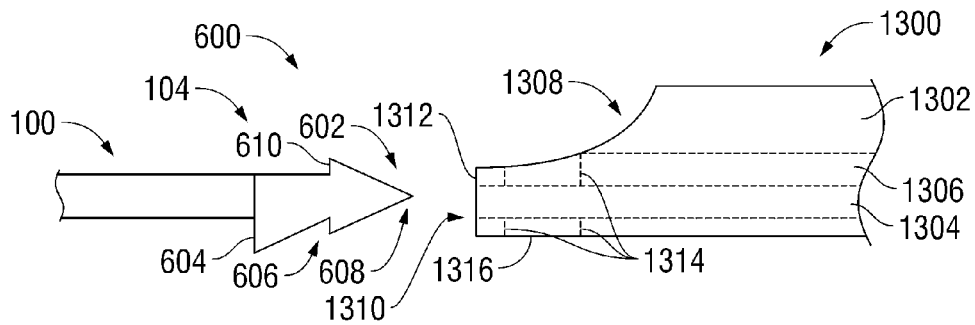
FIG. 4B is a side plan view of the dual-lumen catheter and the coupling of FIG. 4A separated from each other.
Figure 4C:
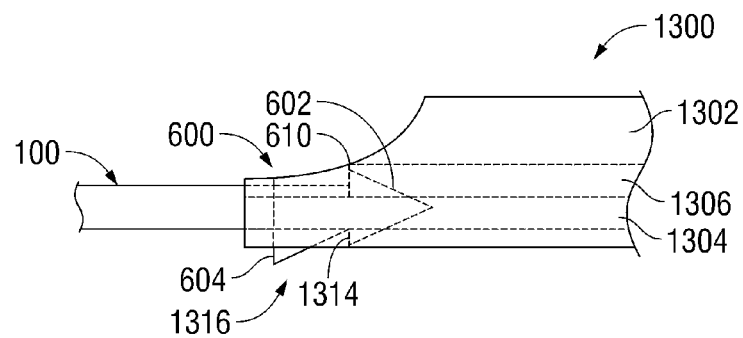
FIG. 4C is a side plan view of the dual-lumen catheter and the coupling of FIG. 4A coupled to each other.

FIGS. 4A-4C illustrate another embodiment of the present disclosure. Coupling 600 is configured for connection to dual-lumen catheter 1300. Dual-lumen catheter 1300 includes first lumen 1302 and second lumen 1304 extending along at least a portion of the length thereof. Septum 1306 divides first and second longitudinal bores 1302, 1304. Moreover, first longitudinal bore 1302 has sealed proximal end 1308, whereas second longitudinal bore 1304 has opening 1312 on the proximal end 1310 thereof. Dual-lumen catheter 1304 additionally includes abutments walls 1314 adapted to support annular supporting wall 610 of coupling 600 and hole 1316 dimensioned to receive barb 604 of coupling 600.

Coupling 600 includes at least one barb 604 extending radially therefrom and pointed end 602 for facilitating insertion into second lumen 1304 of dual-lumen catheter 1300. Pointed end 602 includes proximal end 606 and distal end 608 and has a frustoconical shape. The cross-section of distal end 608 of pointed end 602 is larger than the cross-section of proximal end 606. In turn, the cross-section of proximal end 606 of pointed end 602 is larger than the cross-section of elongate tunneling member 100. Proximal end 606 of pointed end 602 defines an annular supporting wall 610 adapted to abut at least one abutment wall 1314 of dual-lumen catheter 1300. Barb 604 is located proximally with respect to proximal end 606 of pointed end 602 and is dimensioned for reception within hole 1316 of dual-lumen catheter 1300. When barb 604 passes through hole 1316, coupling 600 securely connects elongate tunneling member 100 to dual-lumen catheter 1300.

In use, a clinician couples elongate tunneling member 100 to dual-lumen catheter 1300 by inserting coupling 600 into second longitudinal lumen 1304 through opening 1312. As the clinician advances coupling 600 through second longitudinal lumen 1304, supporting wall 610 engages abutment walls 1314 and barb 604 protrudes out of dual-lumen catheter 1300 through hole 1316. As barb 604 passes through hole 1316 and supporting wall 610 adjoins abutment walls 1314, coupling 600 securely couples dual-lumen catheter 1300 to elongate tunneling member 100. The clinician can then dictate the movement of dual-lumen catheter 1300 through elongate tunneling member 100.

Figure 5A:
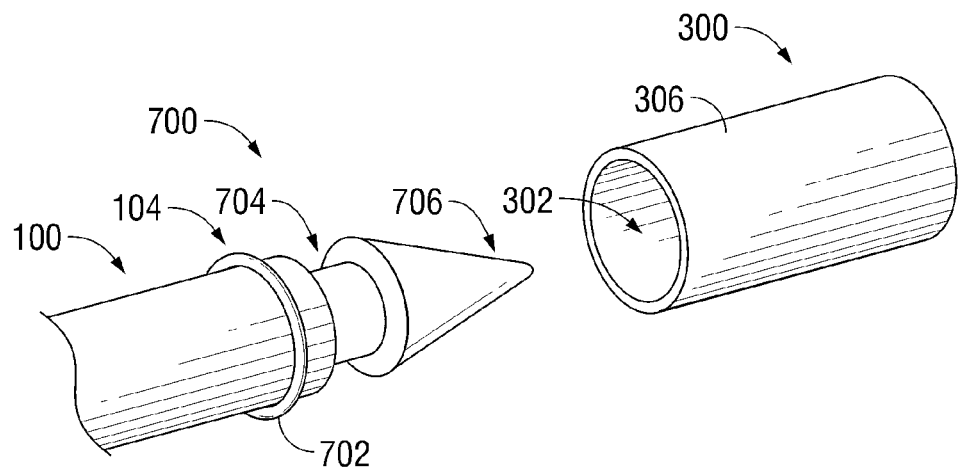
FIG. 5A is a perspective view of an alternate embodiment of a tunneling system including a coupling having a tapered tip, a peripheral recess, and a compression ring.
Figure 5B:
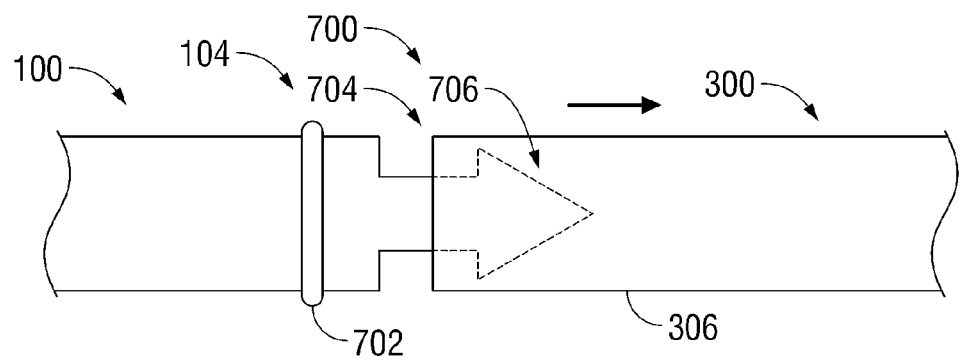
FIG. 5B is a side plan view of the coupling of FIG. 5A with the tapered tip positioned inside a longitudinal lumen of a catheter.
Figure 5C:
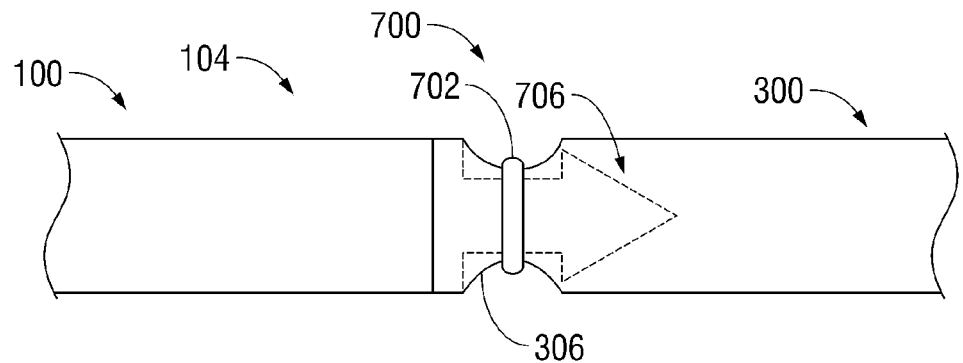
FIG. 5C is a side cross-sectional view of the coupling of FIG. 5A with the compression ring positioned with the peripheral recess.

With reference to FIGS. 5A-5C, another embodiment of elongate tunneling member 100 includes coupling 700 for attaching catheter 300 to elongate tunneling member 100 using compression forces. In this embodiment, the force needed to connect coupling 700 to catheter 300 is less than the force required to disconnect coupling 700 from catheter 300. Coupling 700 is located on the second longitudinal end 104 of elongate tunneling member 100 and incorporates compression ring 702, recess 704 and tapered end 706. Compression ring 702 is biased inwardly toward the longitudinal axis of elongate tunneling member 100 and is slidably positioned on second longitudinal end 104 of elongate tunneling member 100. Recess 704 is located proximally with respect to tapered end 706 and is adapted to receive compression ring 702. Tapered end 706 assists in the insertion of coupling 700 into the longitudinal bore 302 of catheter 300.

During use, a clinician connects elongate tunneling member 100 to catheter 300 by initially positioning coupling 700 inside longitudinal bore 302. Specifically, at least a portion of recess 704 has to be situated in longitudinal bore 302. After placing coupling 700 within longitudinal bore 302, the clinician slides compression ring 702 toward catheter 300. While in motion, compression ring 702 travels along a portion of the outer surface 306 of catheter 300 until it reaches recess 704. When compression ring 702 reaches recess 704, it compresses a portion of outer surface 306 of catheter 300 against recess 704, thereby securing catheter 300 to elongate tunneling member 100 through coupling 700. Once catheter 300 has been coupled to elongate tunneling member 100, the clinician can maneuver catheter 300 by controlling the movement of elongate tunneling member 100.

Figure 5D:
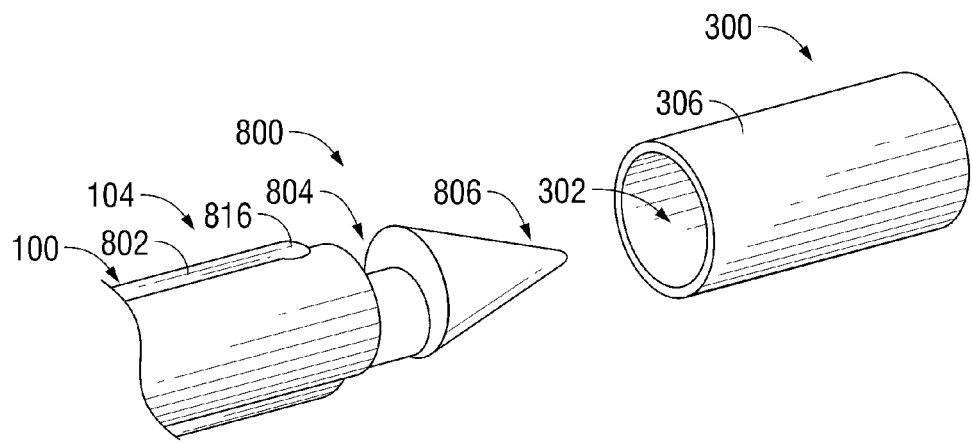
FIG. 5D is a perspective view of another alternate embodiment of the tunneling system including a coupling having a tapered tip, a recess, and a compression sleeve.
Figure 5E:
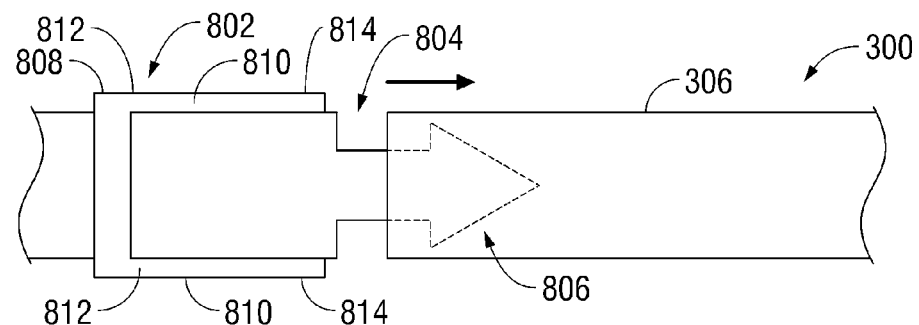
FIG. 5E is a side plan view of the tunneling system of FIG. 5D with the tapered tip inserted in a longitudinal lumen of the catheter.
Figure 5F:
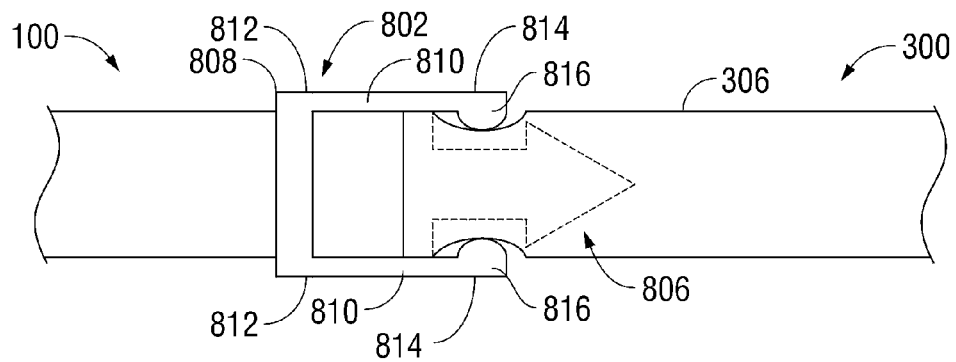
FIG. 5F is a side plan view of the tunneling system of FIG. 5D with locking detents of the compression sleeve engaging the catheter adjacent the recess.

With reference to FIGS. 5D-5F, in a further embodiment, second longitudinal end 104 of elongate tunneling member 100 includes coupling 800 adapted to compress a portion of catheter 300. Coupling 800 contains recess 804, tapered end 806, and compression sleeve 802 slidably positioned on the elongate tunneling member 100. Tapered end 806 has frustoconical shape and facilitates the insertion of coupling 800 into longitudinal bore 302 of catheter 300. Recess 804 is dimensioned to receive at least a portion of compression sleeve 802 and at least a portion of catheter 300. Compression sleeve 802 contains collar 808 and a plurality of axially extending legs 810. Each leg 810 has proximal end 812 and distal end 814. Distal ends 814 of each leg 810 have pressing portions or detents 816 for compressing a portion of a catheter 300 against recess 804. Each distal end 814 is inwardly biased toward the longitudinal axis of elongate tunneling member 100. Although the drawings show compression sleeve 802 having a particular configuration, compression sleeve 802 may have other components. For instance, instead of legs 810, compression sleeve 802 may include a cylindrical elongate structure extending from collar 808 and having inwardly biased detents at a distal end thereof.

In operation, the clinician introduces at least tapered end 806 and recess 805 inside longitudinal bore 302 of catheter 300. Subsequently, the clinician slides compression sleeve 802 toward the recess 804. As compression sleeve 802 moves toward recess 804, detents 816 move along a portion of the outer surface 306 of catheter 300 until they reach the recess 804. When detents 816 reach recess 804, the detents 816 move inwardly toward the recess 804 and press a portion of the outer surface 306 of catheter 300. The compression exerted by detents 816 on the portion of outer surface 306 adjacent to recess 804 effectively secures catheter 300 to elongate tunneling member 100. After connecting catheter 300 to elongate tunneling member 100, the clinician may control the movement of catheter 300 through elongate tunneling member 100.

Figure 6A:
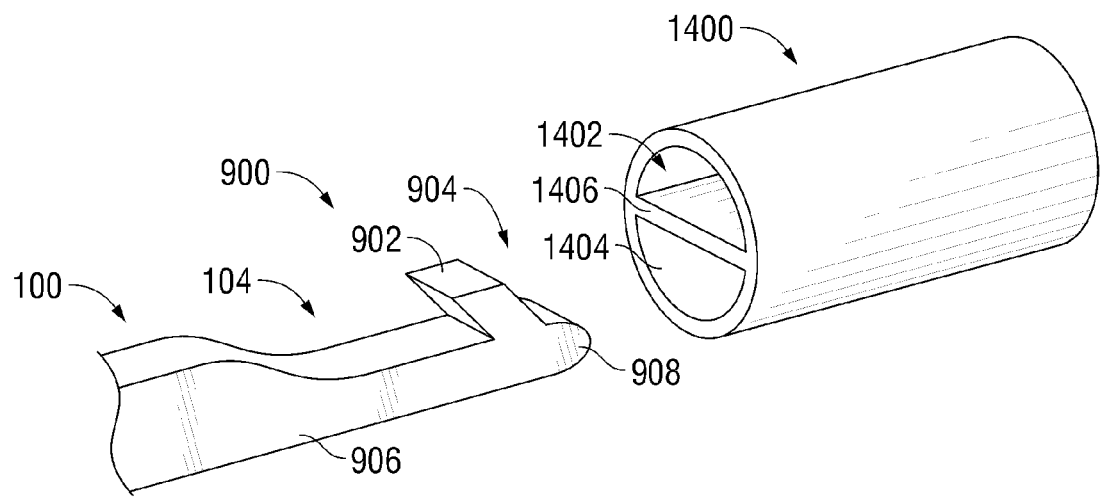
FIG. 6A is a perspective view of another embodiment tunneling system including a coupling having a hook for releasably connecting a dual-lumen catheter.
Figure 6B:
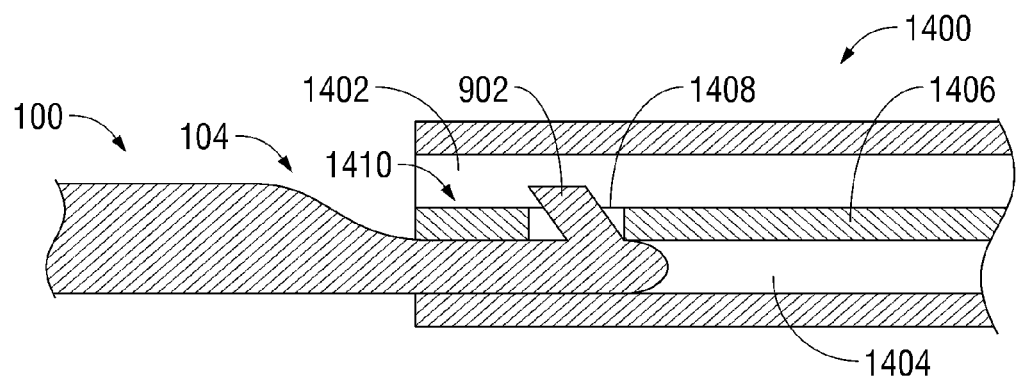
FIG. 6B is a side cross-sectional view of the coupling shown in FIG. 6A attached to the dual-lumen catheter.

With reference to FIGS. 6A-6B, an alternative embodiment of elongate tunneling member 100 includes coupling 900 located on second longitudinal end thereof 104. Coupling 900 is adapted to connect elongate tunneling member 100 to a dual-lumen catheter 1400. Dual-lumen catheter 1400 includes septum 1406 separating first and second longitudinal lumens 1402, 1404. Septum 1406 extends along the length of dual-lumen catheter 1400 and includes aperture 1408 located on proximal portion 1410 thereof. Aperture 1408 forms a passage between first and second longitudinal lumens 1402, 1404 and is dimensioned to receive hook 902 of coupling 900.

Coupling 900 further includes rod 906 with hook 902 positioned at distal end 904 of rod 906. Rod 906 includes distal tip 908 and its cross-section is smaller than the cross-section of elongate tunneling member 100. The cross-section of rod 906 is dimensioned for reception within at least one of the longitudinal lumens 1402, 1404 of dual-lumen catheter 1400. Hook 902 extends radially from rod 906 and is configured to be received in aperture 1408 of dual-lumen catheter 1400. Additionally, hook 902 defines an acute angle with respect to the longitudinal axis of rod 906.

During operation, a clinician positions rod 906 in either of the longitudinal lumens 1402, 1404 of catheter 1400. While rod 906 enters the longitudinal lumen 1402, 1404, hook 902 passes through aperture 1408 thereby coupling elongate tunneling member 100 to dual-lumen catheter 1400. Then, the clinician can maneuver dual-lumen catheter 1400 through a subcutaneous tunnel by directing the movement of elongate tunneling member 100.

Figure 7A:
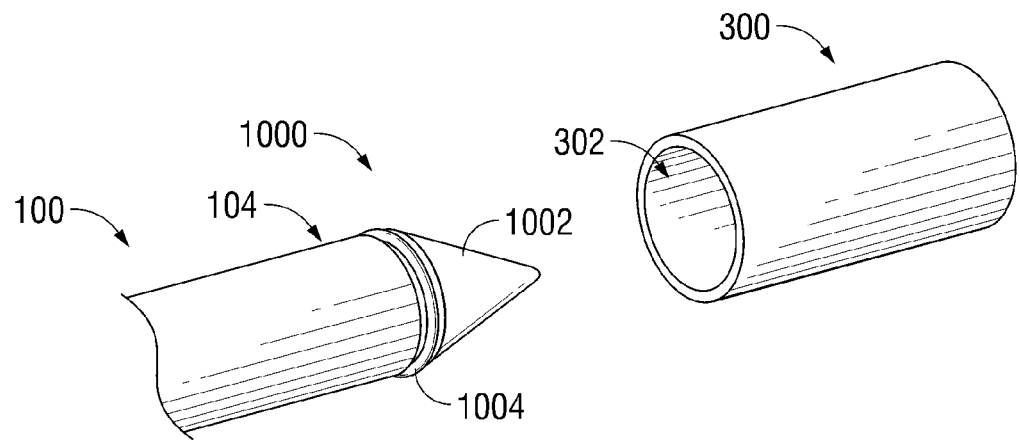
FIG. 7A is a perspective view of another embodiment of the tunneling system including a coupling having an expansion ring disposed in an annular groove and a tapered tip dimensioned for reception within a longitudinal bore of a catheter.
Figure 7B:
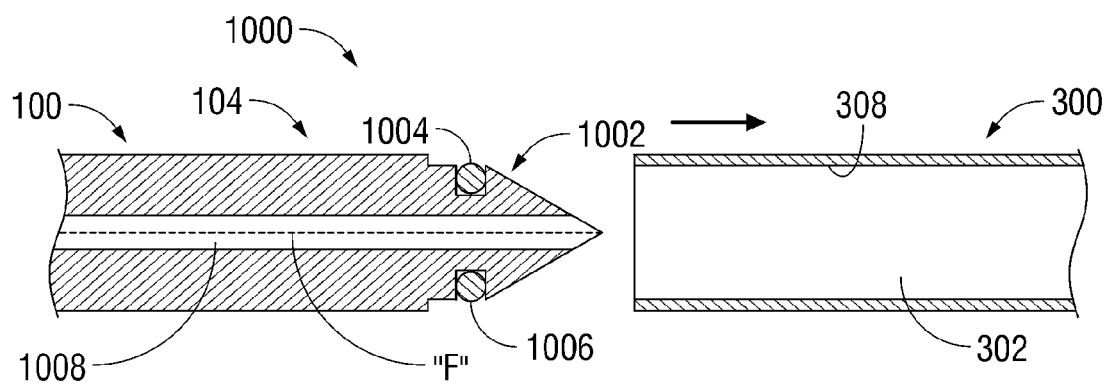
FIG. 7B is a side cross-sectional view of the tunneling system of FIG. 7A and the catheter.
Figure 7C:
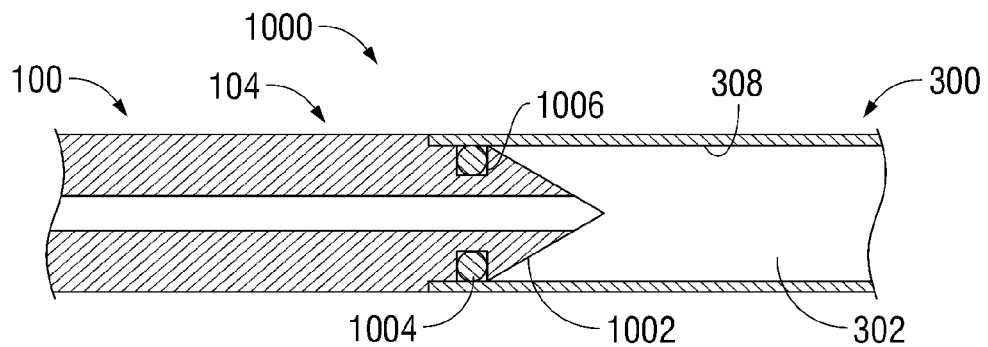
FIG. 7C is a side cross-sectional view of the tunneling system of FIG. 7A connected to a catheter.

Referring now to FIGS. 7A-7C, another embodiment of tunneling member 100 incorporates coupling 1000 for connecting elongate tunneling member 100 to catheter 300 by applying pressure to an inner surface 308 of catheter 300. Coupling 1000 is disposed adjacent second longitudinal end 104 of elongate tunneling member 100 and includes lumen 1008 extending therethrough, tapered distal tip 1002, expanding ring 1004, and annular groove 1006 adapted to receive the expanding ring 1002. Tapered distal tip 1002 is located distally with respect to annular groove 1006 and assists the insertion of coupling 1000 into longitudinal bore 302 of catheter 300. Annular groove 1006 spans the circumference of coupling 1000 and is configured to receive expanding ring 1004. Expanding ring 1004 is securely positioned in annular groove 1006 but is biased outwardly relative to the longitudinal axis of elongate tunneling member 100. Expanding ring 1004 may be fabricated from a suitable elastomer, foam, bladder, etc. It is further envisioned that expandable ring may be adapted to swell in the presence of liquids, e.g., have absorption characteristics which causes ring 1004 to expand when exposed to fluids such as blood or other bodily fluids. Lumen 1008 may be used to flush catheter 300 subsequent to mounting to the catheter 300 and may be in fluid communication with a fluid source. Fluid flow is represented schematically as flow "F". It is further envisioned that the fluids transferred through lumen 1008 may assist in the expansion of expanding ring 1004.

During use, the clinician inserts coupling 1000 into longitudinal bore 302 of catheter 300. While coupling 1000 advances through longitudinal bore 302, expanding ring 1004 applies pressure to the inner surface 308 of catheter 300. The pressure applied to inner surface 308 by expanding ring 1004 establishes a secured relation between elongate tunneling member 100 and catheter 300. Once catheter 300 has been properly secured to elongate tunneling member 100, the clinician can maneuver catheter 300 through elongate tunneling member 100.

Figure 7D:
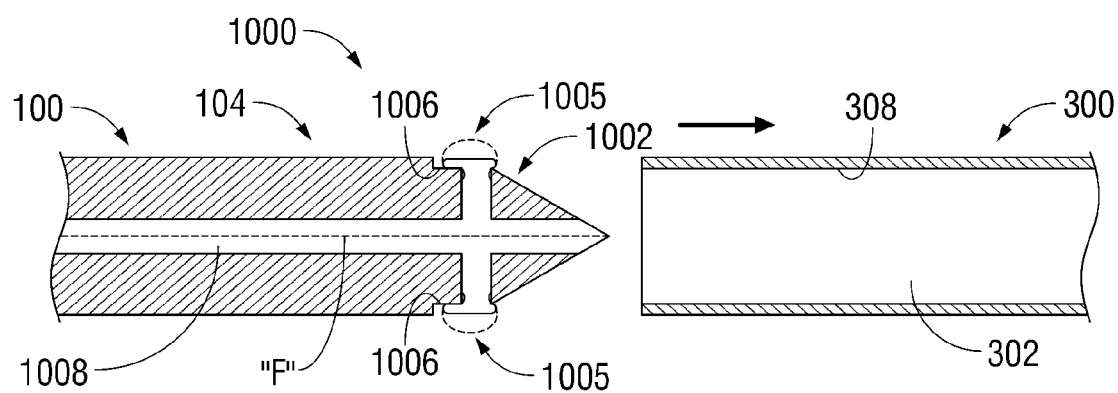
FIG. 7D is a side cross-sectional view of a tunneling system according to another embodiment of the present disclosure.

With reference to FIG. 7D, another embodiment of tunneling member 100 is illustrated. In accordance with this embodiment, coupling 1000 incorporates an inflatable member or balloon 1005 in lieu of expanding ring 1004. Inflatable balloon 1005 may be disposed within annular groove 1006, or, in the absence of the groove 1006, mounted about the outer surface of the coupling 1000. Inflatable member 1005 is in fluid communication with lumen 1008 extending the length of tunneling member 100. During operation, the clinician introduces coupling 1000 within catheter 300. Thereafter, fluid is passed through lumen 1008 to inflate inflatable member 1005. (see phantom lines) As inflatable member 1005 expands, the outer surfaces of inflatable member 1005 engage the inner surfaces of catheter 300, thereby securing tunneling member 100 to catheter 300.

Figure 8:
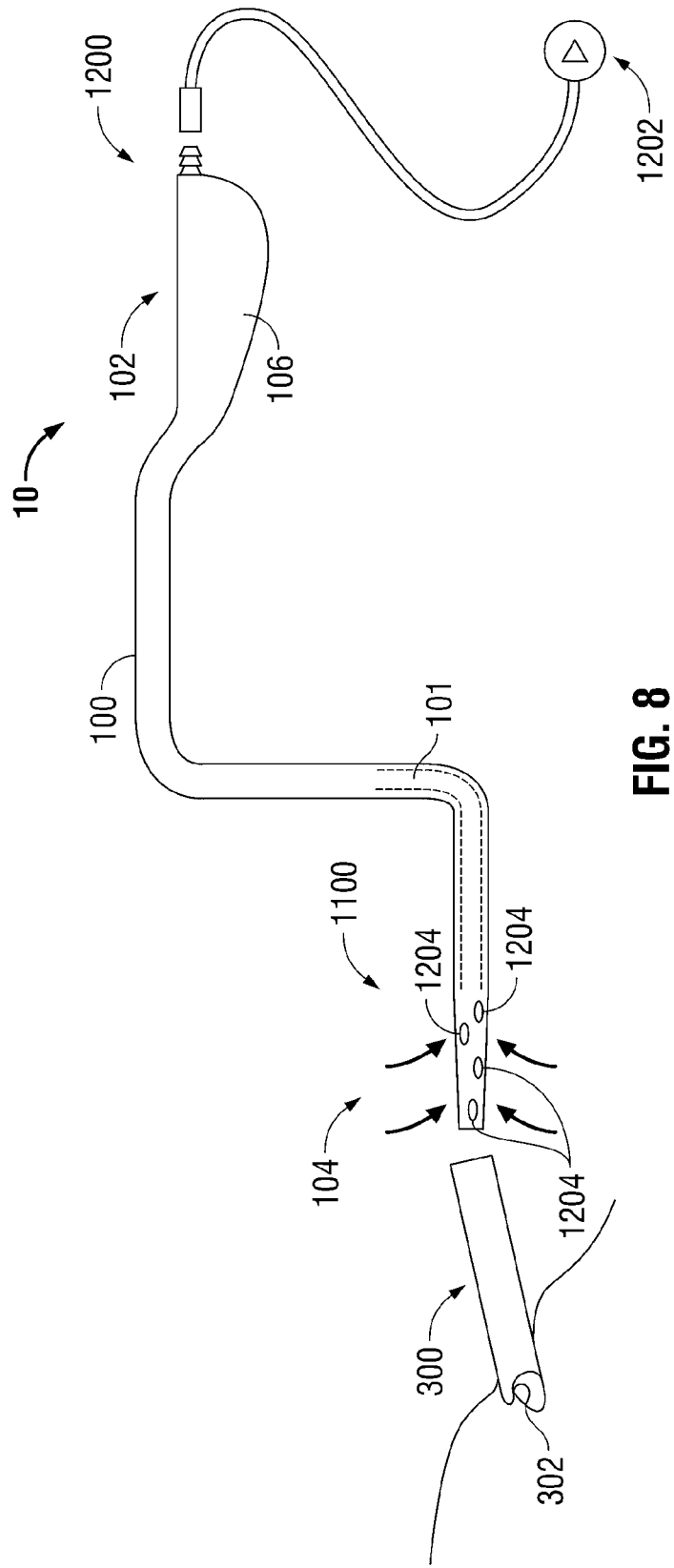
FIG. 8 is a perspective view of a tunneling system having a pneumatic system configured to hold a portion of the catheter.

With reference to FIG. 8, an embodiment of tunneling system 10 contains pneumatic system 1200 configured to hold catheter 300. Pneumatic system 1200 includes suction source 1202 operatively connected to elongate tunneling member 100 and a plurality of ports 1204 disposed about coupling 1100. A tube 1206, or any other suitable apparatus, interconnects suction source 1202 and elongate tunneling member 100, and maintains fluid communication between suction source 1202 and a longitudinal bore 101 (shown in phantom) extending through elongate tunneling member 100. Elongate tunneling member 100 includes handle 106 on its first longitudinal end 102 and coupling 1100 on its second longitudinal end 104. Coupling 1100 incorporates ports 1204 and is dimensioned for reception within longitudinal bore 302 of catheter 300. Ports 1204 are in fluid communication with the longitudinal bore (not shown) of elongate tunneling member 100 and suction source 1202. During use, suction source 1202 supplies suction force to pneumatic system 1200.

In operation, the clinician initially positions coupling 1110 along with ports 1204 inside longitudinal bore 302 of catheter 300. Then, the clinician turns on suction source 1202 to provide ports 1202 with the suction force needed to hold catheter 300. When suction source 1202 is activated, pneumatic system 1200 sucks fluid from within catheter 300 through ports 1204 and the suction forces exerted in longitudinal bore 302 draw the internal wall surfaces of the catheter 300 onto coupling 1110 to thereby secure the catheter 300 to elongate tunneling member 100.

Figure 9:
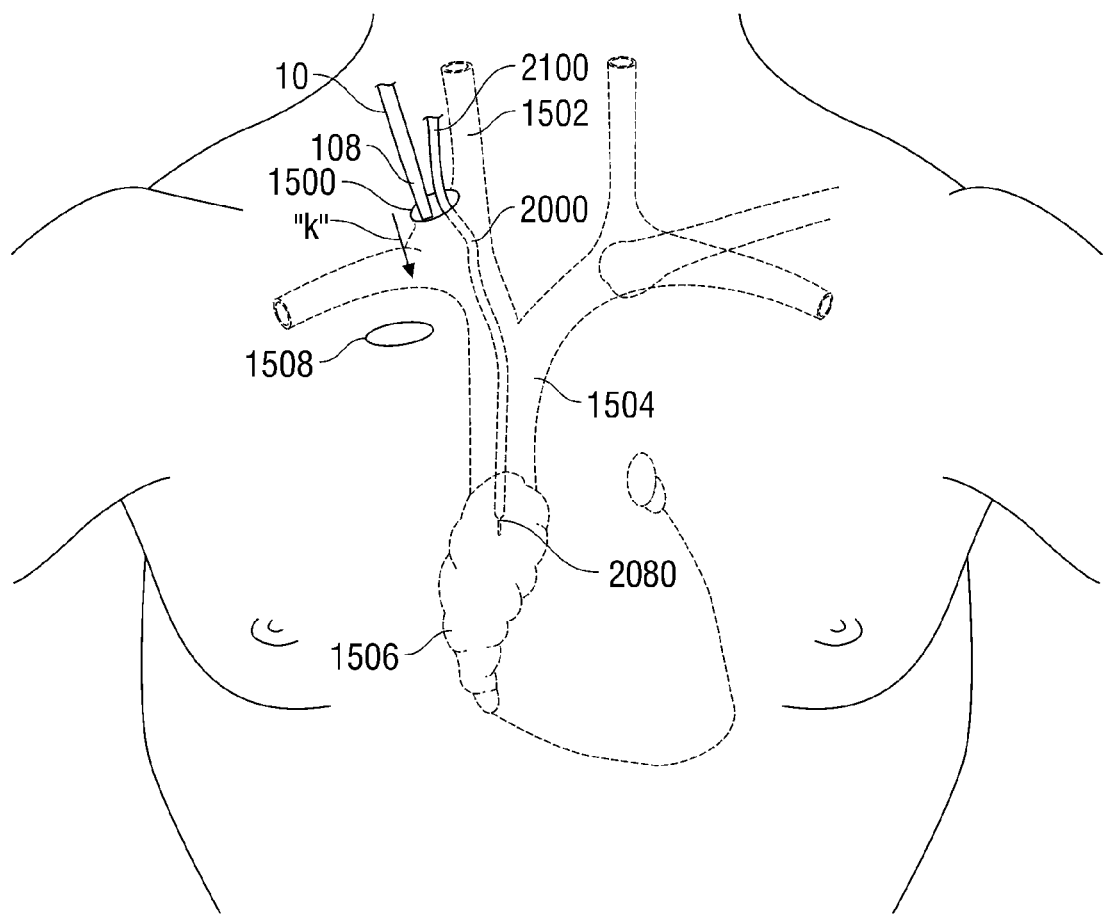
FIGS. 9-10 are front plan views of the chest area of a subject illustrating the steps of a reverse tunneling procedure.

As discussed above, any of the embodiments of the presently disclosed tunneling system 10 may be utilized during a reverse tunneling procedure. In this procedure, tunneling system 10 creates or enlarges a subcutaneous tunnel for deploying any suitable catheter inside the right atrium through the right jugular vein. As appreciated, the catheter 2000 may be implanted in the right atrium via the left jugular vein, the right atrium through the right subclavian vein, the right atrium through the left subclavian vein, or implanted in the femoral vein of the subject. With reference to FIG. 9, the internal jugular vein 1502 is punctured using known techniques. A guide wire may be positioned to access the heart to facilitate insertion of the leading end 2080 of catheter 2000 within the heart through techniques known in the art. An entry opening or venotomy 1500 is made above the clavicle, through the skin and the subcutaneous tissue. Distal end 2080 of catheter 2000 is inserted through the internal jugular vein 1502, the superior vena cava 1504 and into the right atrium 1506. The positioning of leading end 2080 of catheter 2000 may be confirmed with an x-ray if desired. Proximal trailing end 2100 of the catheter 2000 may extend from the venotomy site 1500.

Once distal leading end 2080 of catheter 2000 is in position, attention is directed to preparing the subcutaneous tunnel incorporating the tunneling approach from the venotomy site 1500 to an exit opening 1508. Exit opening 1508 is made adjacent to the chest wall below the venotomy site 1500 to define one base of the tunnel. Thereafter, an optional dilator element may be mounted to the tunneling system 10. Offset segment 108 of tunneling system 10 may be introduced within the venotomy site 1500 and advanced toward exit opening 1508. As tunneling system 10 is advanced toward the exit opening 1508, the dilator element engages internal tissue beneath the venotomy site 1500. An enlarged tissue tract is thereby made to create a shelf for accommodating a cuff of the catheter by advancing the dilation element a predetermined distance through the venotomy site 1500 toward the exit opening 508. The predetermined distance corresponding to the desired location of the cuff 210. Tunneling system 10 is then retracted to the venotomy site 1500 and the dilator element is removed from the tunneling system 10.

Figure 10:
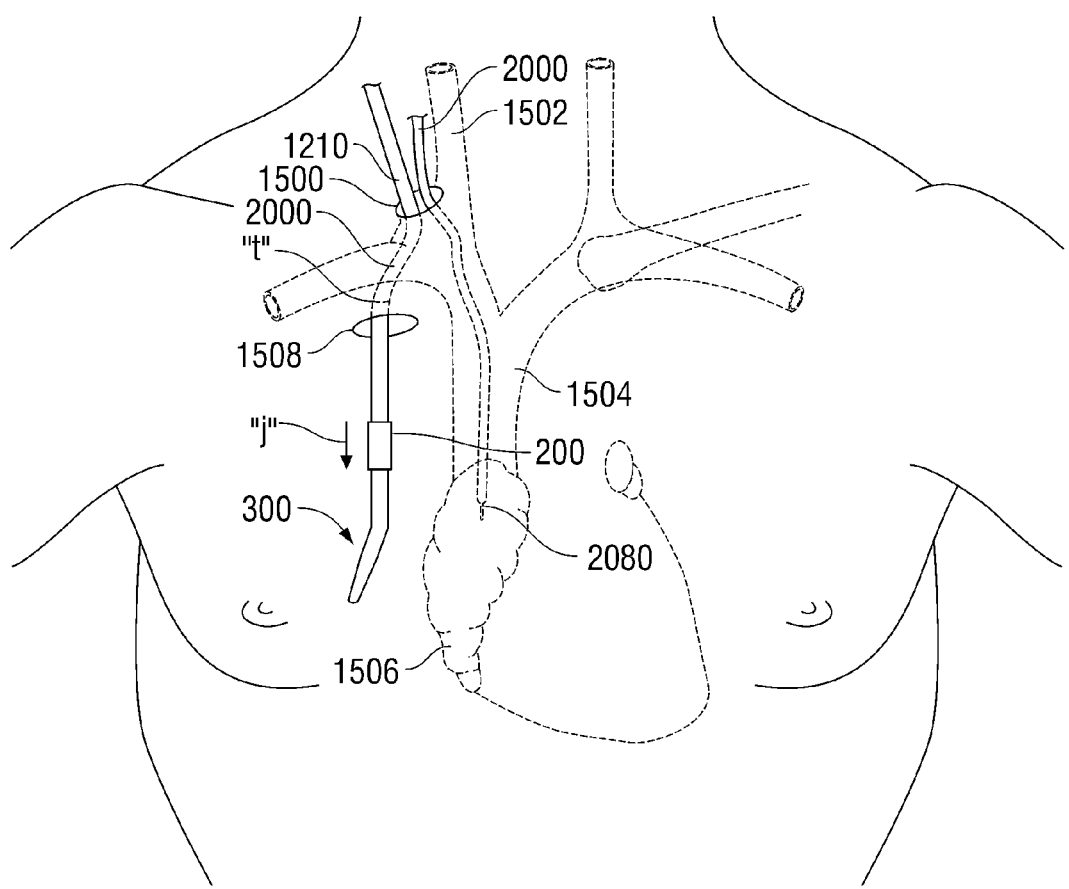

Referring now to FIG. 10, coupling 200, or any of the other disclosed couplings, is then connected to the catheter 2000 to secure the catheter 200 to the tunneling system 10. Once the catheter 2000 is secured, tunneling system 10 is readvanced in the direction of directional arrow "j" from the venotomy site 1500 toward the exit opening 1508 until the ends of catheter 2000 is exposed from the exit opening 1508. The relatively small profile of the coupling 200 facilitates passage of the coupling 200 through tissue. The catheter 2000 is removed from its mounting to tunneling system 10 and assembled in order to be connected to a hemodialysis machine. In one embodiment, catheter 2000 is released from its mounting to coupling 200 by exerting a linear force on catheter 2000. Alternatively, with a more permanent connection with coupling 200, the catheter 2000 is severed or cut adjacent the coupling 200 to expose the catheter ends.

Figure 11:
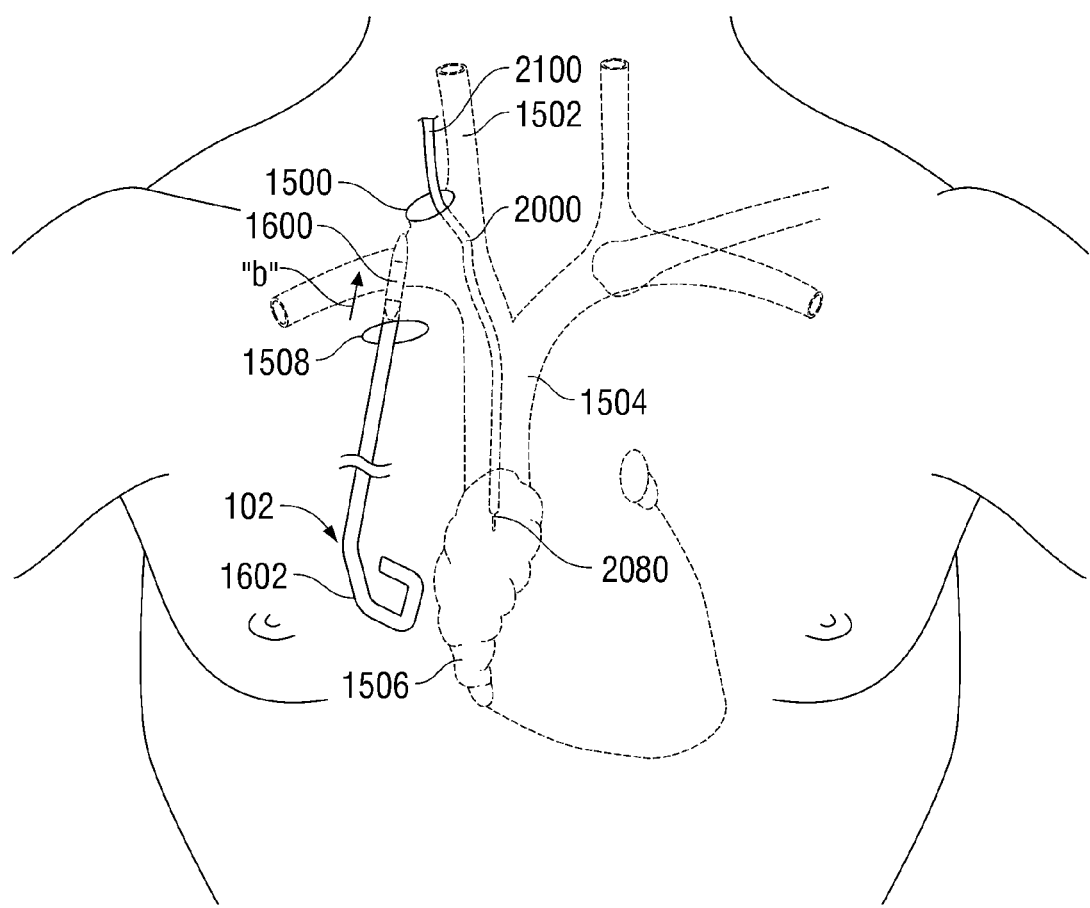
FIGS. 11-12 are front plan views of the chest area of a subject showing the steps of an alternative reverse tunneling procedure.
Figure 12:
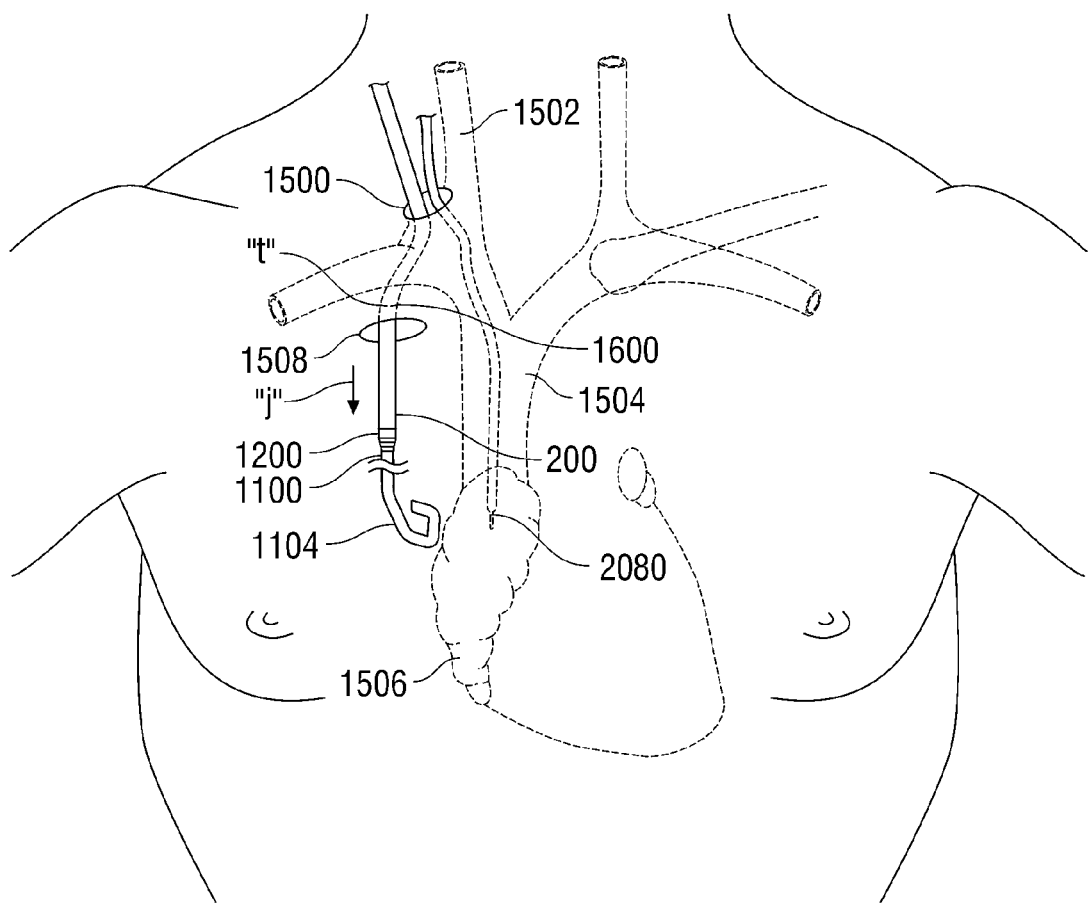

With reference to FIGS. 11 and 12, clinician may also perform an alternative reverse tunneling procedure with elongate tunneling system 10. In this reverse tunneling procedure, the clinician punctures the internal jugular vein 1502 with any conventional surgical tool. A guide wire may be positioned to access the heart to facilitate insertion of the leading end 2080 of catheter 20000 within the heart through techniques known in the art. The clinician makes an entry opening or venotomy 1500 above the clavicle. The entry opening 1500 should extend through the skin and the subcutaneous tissue of the subject. After venotomy, the clinician inserts the leading end 2080 of the catheter 2000 in the right atrium 1506 as explained above for the other reverse tunneling procedure. The trailing end 2100 of the catheter 2000 may extend from the venotomy site 1500.

Following the placement of the leading end 2080 catheter 2000 in the right atrium 1506, the clinician creates an exit opening 1508 below the venotomy site 1500. The exit opening 1508 should extend through the skin and the subcutaneous tissue of the subject. Thereafter, the clinician may place releasable cover 1600 over the coupling 200 of the elongate tunneling system 10. The clinician subsequently grabs the elongate tunneling system 10 by the handle 1602 and advances the elongate tunneling system 10 from the exit opening 1508 toward the entry opening 1500 as indicated by arrow "b." While the clinician moves the elongate tunneling system 10 from exit opening 1508 toward entry opening 1500, the elongate tunneling member 100 creates or enlarges a subcutaneous tunnel between the two openings. The clinician may subcutaneously advance elongate tunneling member 10 until the releasable cover 1600 is exposed through entry opening 1500. Afterwards, the clinician removes the releasable cover 1600 and couples the trailing end 2100 of the catheter 2000 to the elongated tunneling system 10 with coupling 200. The elongate tunneling system 10 is the retracted, along with the catheter 200, from the entry opening 1500 toward the exit opening 1508, in the direction indicated by arrow "j," until the trailing end 2100 of the catheter 2000 is exposed through exit opening 1508. The catheter 2000 is removed from its mounting to tunneling system 10 and assembled to be connected to a hemodialysis machine. In one embodiment, catheter 2000 is released from its mounting to coupling 200 by exerting a linear force on catheter 2000. Alternatively, with a more permanent connection with coupling 200, the catheter 2000 is severed or cut adjacent the coupling 200 to expose the catheter ends. Further details of the reverse tunneling procedures may be ascertained by reference to U.S. patent application Ser. No. 12/041,422, filed Mar. 3, 2008, the entire contents of which is hereby incorporated by reference herein.

It will be understood that various modifications may be made to the embodiments disclosed herein. Therefore, the above description should not be construed as limiting, but merely as exemplifications of the embodiments. Those skilled in the art will envision other modifications within the scope and spirit of the present disclosure.

What is claimed is:

1. A tunneling system comprising:
    a catheter having a proximal end, a distal end, first and second longitudinal lumens separated by a septum, and at least one hole extending through the septum from the first longitudinal lumen to the second longitudinal lumen and providing passage between the first and second lumens, the at least one hole being spaced from the proximal end of the catheter; and
    an elongate tunneling member defining a longitudinal axis along at least a portion of a longitudinal length thereof, the elongate tunneling member having a first end and a second end, the second end including a coupling segment integrally formed therewith, the coupling segment adapted for at least partial reception within at least one of the longitudinal lumens of the catheter, and wherein the coupling segment includes at least one protrusion adapted to be received within the at least one hole extending through the septum to secure the catheter to the tunneling member.

2. The tunneling system according to claim 1, wherein the at least one protrusion includes a hook adapted to engage the hole extending through the septum.

3. The tunneling system according to claim 2, wherein the hook defines an acute angle with respect to the longitudinal axis defined by the elongate tunneling member.

4. The tunneling system according to claim 2, wherein the hook extends toward the proximal end of the catheter when the coupling segment is received within the at least one hole extending through the septum.

5. The tunneling system according to claim 1, wherein the first and second longitudinal lumens are D-shaped lumens.

6. The tunneling system according to claim 1, wherein the coupling segment is adapted for at least partial reception in either of the first and second longitudinal lumens.

* * * * *